US008419699B2

(12) United States Patent
Giloh

(10) Patent No.: US 8,419,699 B2
(45) Date of Patent: Apr. 16, 2013

(54) ABSORBENT PAD

(75) Inventor: Tamar Giloh, Manchester (GB)

(73) Assignee: Tamicare, Ltd., Manchester (GB)

( * ) Notice: Subject to any disclaimer, the term of this patent is extended or adjusted under 35 U.S.C. 154(b) by 493 days.

(21) Appl. No.: 12/257,623

(22) Filed: Oct. 24, 2008

(65) Prior Publication Data

US 2010/0106124 A1    Apr. 29, 2010

(51) Int. Cl.
*A61F 13/15* (2006.01)

(52) U.S. Cl.
USPC .................................................. 604/385.01

(58) Field of Classification Search .......... 604/393–396, 604/402
See application file for complete search history.

(56) References Cited

U.S. PATENT DOCUMENTS

| | | | |
|---|---|---|---|
| 4,526,825 A | 7/1985 | Whitehead | |
| 4,554,191 A | 11/1985 | Korpman | |
| D288,850 S | 3/1987 | Ziegler et al. | |
| 4,834,739 A | 5/1989 | Linker, III et al. | |
| 5,304,161 A | 4/1994 | Noel et al. | |
| 5,849,805 A | 12/1998 | Dyer | |
| D431,293 S | 9/2000 | Finkle et al. | |
| 6,475,203 B1 | 11/2002 | Rubio | |
| D478,167 S | 8/2003 | Proglhof | |
| D482,444 S | 11/2003 | Ribeiro de Carvalho et al. | |
| D486,228 S | 2/2004 | Fonseca et al. | |
| D492,408 S | 6/2004 | Proglhof | |
| 6,908,456 B1 | 6/2005 | Drevik | |
| D523,957 S | 6/2006 | Persson | |
| D528,656 S | 9/2006 | Glaug et al. | |
| 2004/0002686 A1 * | 1/2004 | Glasgow et al. | 604/300 |
| 2004/0040650 A1 | 3/2004 | Venturino et al. | |
| 2004/0073180 A1 * | 4/2004 | Strannemalm | 604/349 |
| 2006/0142722 A1 | 6/2006 | Koenig et al. | |

FOREIGN PATENT DOCUMENTS

| | | |
|---|---|---|
| EP | 1 133 961 A1 | 9/2001 |
| FR | 1 300 011 A | 7/1962 |
| WO | 2007/061341 A1 | 5/2007 |
| WO | WO 2007061341 A1 * | 5/2007 |
| WO | 2007/069966 A1 | 6/2007 |
| WO | 2008/127152 A1 | 10/2008 |

* cited by examiner

*Primary Examiner* — Melanie Hand

(74) *Attorney, Agent, or Firm* — McDonnell Boehnen Hulbert & Berghoff LLP

(57) ABSTRACT

An absorptive pad having a frontward pad section and a rearward pad section of sufficient length to cover the buttocks of a user to thereby control rearward leakage of fluid. The width of the rearward pad section is less than the width of the frontward pad section, and may become increasingly narrower until the rear edge of the absorptive pad. This ergonomic shape of the pad allows for the absorptive pad to feel comfortable to the user while providing adequate protection from rearward leakage.

9 Claims, 1 Drawing Sheet

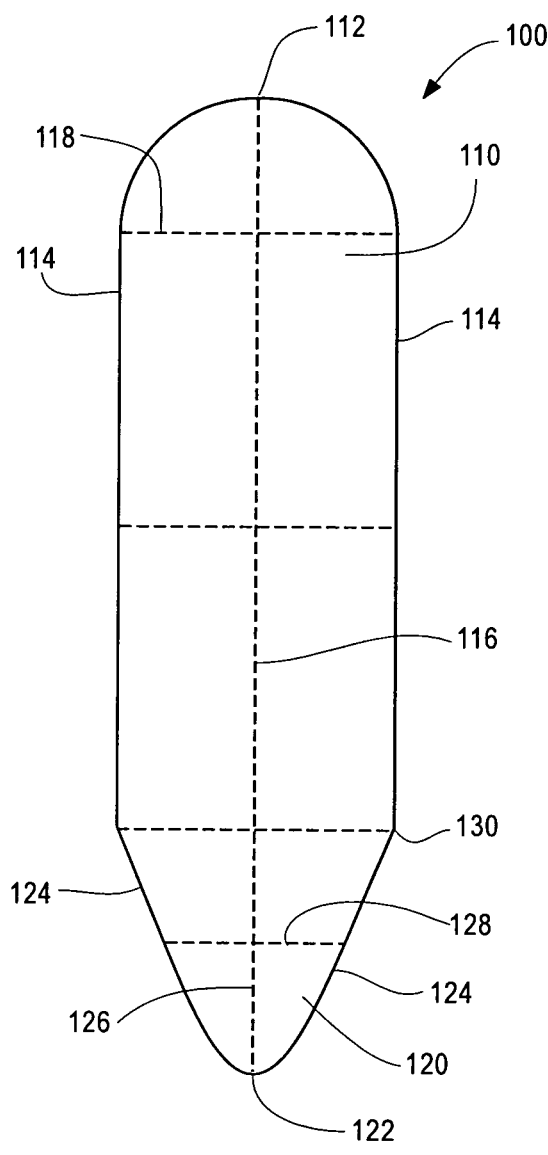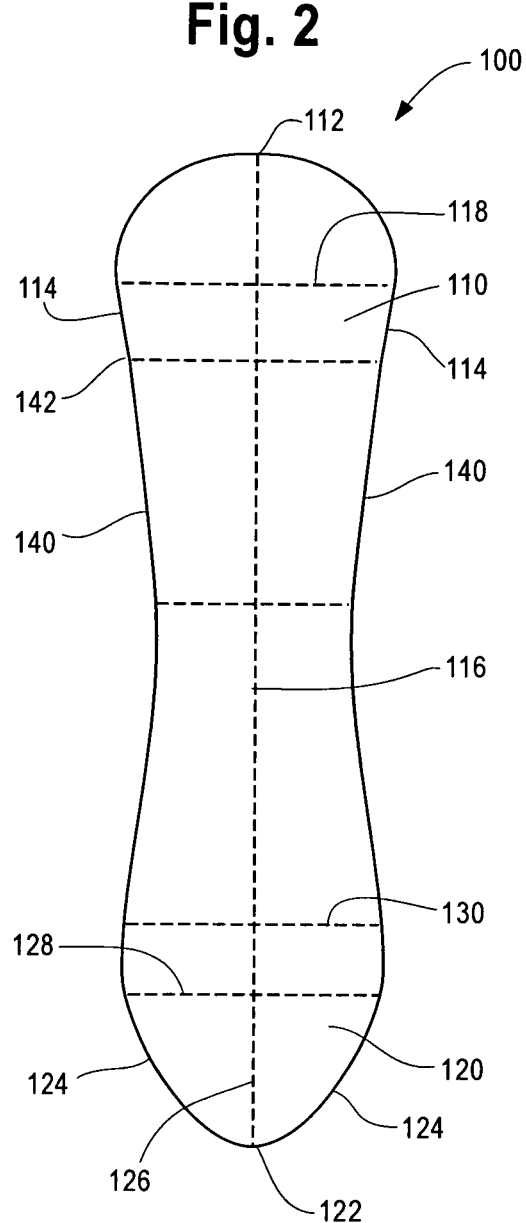

ABSORBENT PAD

FIELD OF THE INVENTION

The present invention relates to absorbent articles generally, and more specifically, to absorbent pads.

BACKGROUND OF THE INVENTION

It is known and described in the art that body liquids, such as urine or blood, are transferred to the back of the body, toward the buttocks. The transfer toward the back of the body is especially likely while an individual is sitting or lying in a non-prone position. Fluids distributed tend to go beyond the rear edge of a conventional pad, causing leakage.

Conventional absorbent pads, mostly for feminine hygiene and adult incontinence products, either provide insufficient coverage and allow for rearward leakage, or are too large and bulky and hence uncomfortable for the wearer. It is known that users of absorbent pads can feel uncomfortable after prolonged use of the pad even though the absorbent capabilities of the pad have not yet been exhausted. The discomfort experienced with the bulky pads is due in large part to the way conventional pads are shaped.

The discomfort experienced while wearing a pad long enough to protect a user from rearward leakage may deter a user from wearing the pad. Accordingly, there remains a need for an improved absorbent pad that protects wearers from rearward leakage and provides greater comfort relative to conventional absorbent pads.

SUMMARY OF THE INVENTION

In one embodiment, the invention provides an absorptive pad having a wider forward pad section and a relatively narrower rearward pad section that is adapted to be worn over the buttocks of a user. The forward pad section is separated from the rearward pad section at a location. The forward pad section has a front edge and a forward width between forward side edges. The rearward pad section has a rear edge and a rear width between rear side edges. The forward pad section comprises a forward pad length measured from the front edge along the longitudinal dimension to the location of the absorptive pad that delineates the forward pad section from the rearward pad section. The rearward pad section has a rear length that is measured along the longitudinal dimension from the rear edge to the location of the absorptive pad. The rearward pad section is integral with the forward pad section.

In another embodiment, the invention provides an article comprising an absorptive pad with a wider forward pad section and a relatively narrower rearward pad section that is adapted to be worn over the buttocks of a user.

Specific preferred embodiments of the invention will become evident from the following more detailed description of certain preferred embodiments and the claims.

BRIEF DESCRIPTION OF THE DRAWINGS

FIG. 1 shows a plan view of an exemplary absorbent pad.
FIG. 2 shows a plan view of an exemplary absorbent pad.

DETAILED DESCRIPTION OF THE INVENTION

Specifically, the invention provides for an absorbent pad intended to prevent the rearward leakage of fluid that is also ergonomically shaped such that it is comfortable to the wearer. The pad provides significant improvement in product performance, efficiency, and discreetness while not hindering the wearer's movability or comfort. The absorptive pad can be worn by an individual to prevent leakage of body fluids, including, but not limited to urine, blood, plasma, menses, and serum. The absorptive pad can be designed for feminine hygiene (e.g. a pad designed to absorb and prevent leakage of menses) or for incontinence (e.g. a pad designed to absorb and prevent leakage of body fluids). Absorptive pad 100 is made to be attached to an article worn by a user, so that absorptive pad 100 may catch and contain any of the aforementioned fluids.

In one embodiment, as shown in the plan view of FIG. 1, absorptive pad 100 comprises a body formed of a forward pad section 110 and a rearward pad section 120. A location 130 separates forward pad section 110 from rearward pad section 120. Forward pad section 110 comprises a front edge 112, forward side edges 114, and a forward pad length 116. Forward pad length 116 is measured in the longitudinal dimension from front edge 112 to location 130. A forward width 118 comprises the width between forward side edges 114. Rearward pad section 120 comprises a rear edge 122 and rear side edges 124. Rearward pad section 120 has a rear length 126 measured from rear edge 122 to location 130 along the longitudinal dimension. A rear width 128 comprises the width between rear side edges 124.

Forward pad section 110 is integral with rearward pad section 120. The length of absorptive pad 100 is such that at least a portion of rearward pad section 120 covers the buttocks of the user when absorptive pad 100 is affixed to an article on the user. The length of absorptive pad 100 may be at least 33 cm. A pad length of 36 cm has been found to particularly useful. Forward width 118 of forward pad section 110 may be of the standard size of absorptive pads as currently used in the art. Generally, forward width 118 is not less than 6 cm. For example, forward width 118 may be within the range of 6 cm to 10 cm. Alternatively, forward width 118 is not limited to this range, and may comprise a number of other ranges. Forward width 118 may decrease in a continuous manner from front edge 112 to location 130.

Because the pad reaches the upper end of the buttocks, the traditional wide shape of the pad feels bulky to a user and tends to create a sweating reaction with the user's skin. Rear width 128 of pad 100, however, is a smaller width than forward width 118 and is sized and shaped so as to provide the user with a comfortable and ergonomic fit as the rearward portion fits against a user's buttocks. Rear width 128 of rearward pad portion 120 comprises a width such that the pad covers at least a portion of each buttock, as well as the crease between the buttocks. Rear width 128 should be large enough to prevent rear side edges 124 of pad 100 from sliding into and resting within the crease between the buttocks. The pad width in rear portion 120 decreases gradually to allow the fluids to distribute longitudinally without interruption. Rear width 128 does not have a consistent width throughout the length of rear length 126, but comprises a varying width. Rear width 128 may decrease in a continuous manner along the longitudinal dimension, from location 130 to rear edge 122. Rear width 128 may comprise a width that is no less than 5 cm at location 130. Rear width 128 may decrease gradually until the width is approximately 1 cm at rear edge 122.

Front edge 112 may be rounded. Alternatively, front edge 112 may be straight. Rear edge 122 may be rounded. Alternatively, rear edge 122 may be straight.

In an alternative embodiment as shown in FIG. 2, a portion of each of forward side edges 114 may form a concave curve 140. A transition point 142 along each of the side edges 114 starts the formation of concave curve 140.

The absorptive pad of the invention may be a protective pad that is generally thinner, lighter, more comfortable, and permits greater maneuverability for the wearer than conventional pads. Because the rear width is decreased, less material of absorptive pad 100 will be brushing against the user's buttocks while the pad is in use, allowing for greater comfort and decreasing the feeling that the user is wearing a diaper. Furthermore, because of the fixed width ratio between the frontward and rearward portions of the pad, the rearward portion will not go between the wearer's buttocks during use and cause greater wearer discomfort.

Any suitable absorptive material may be used in the absorptive pad. In one embodiment, the absorptive pad 100 may comprise one or more layers of an absorptive material such as cotton, pulp, or airlaid.

In another embodiment, the absorptive pad 100 may comprise a plurality of functional zones. The zones can be different heights at different locations on the surface of the pad, for example by using fibers of various lengths or particles of various heights. Also, the zones can differ in density. For example, a zone with zero density (e.g. no fibers) can serve to control flow of fluids by surface tension along the edges of the zone. In addition, a wicking zone connected to a zero density zone can increase fluid flow speed to a desired location on the article. In a particular embodiment, absorptive pad 100 can be designed to provide areas of distribution in places that are most likely to contact body fluids. For example, the distribution and absorptive zones can be positioned differently depending on whether a male or female will be wearing the pad.

Absorptive areas can be created by lateral application of various types of particles, such as fluff; super absorbent fibers (SAF); treatment material to treat existing conditions or prevent infection (including, but not limited to antibiotics, antifungal compounds, antiviral compounds, and analgesics); diagnostic material (including, but not limited to compounds that test for chemical adulterants, pH indicators, and labeled antibodies); odor control material; liquid absorbing particulate gels; odor absorbing gels; or any other absorbent material. The absorptive areas can be designed to form any desired pattern and size in a lateral or vertical dimension relative to the article. In one embodiment, an absorptive area can comprise absorptive particles that are contained in a liquid permeable material to ensure the particle remain in a discrete location. For example, absorptive particles can be contained in a mesh container, and the container can be attached (e.g. glued) to a surface.

In another embodiment, the pad may further comprise a liquid impermeable barrier layer to prevent leakage of fluids onto the wearer's garments. Suitable but not limiting examples of barrier layers include rubber and wax. The bottom of pad 100 may comprise a layer of adhesive material, or areas of adhesive materials, so that pad 100 may be affixed to an undergarment.

In another embodiment, the absorbent pad may be affixed onto a protective undergarment such as the ones described in Giloh et al. U.S. Pat. No. 6,987,210, issued Jan. 17, 2008 and U.S. Pat. No. 7,354,424, issued Apr. 8, 2008 (Tamicare Ltd, assignee), which is incorporated by reference in its entirety.

In still another embodiment, absorptive pad may comprise an adjustment device, such as an adhesive flap, or the like, that can be integral with the pad. An adjustment device can provide a means for making an article of the invention fit more snugly on the article that is worn by the user. Representative examples are described in U.S. Pat. No. 7,354,424, issued Apr. 8, 2008 (TamiCare Ltd., assignee).

It will be appreciated by persons skilled in the art of that the present invention is not limited by what has been particularly shown and described hereinabove. Rather the scope of the present invention includes variations and modification of the various features described in the specification and shown in the drawings which may occur to a person of ordinary skill in the art upon reading the foregoing description and which are not in the prior art.

What is claimed is:

1. An absorptive pad having a wider forward pad section and a relatively narrower rearward pad section that is adapted to be worn over the buttocks of a user;
   the forward pad section having a front edge and a forward width between forward side edges;
   the rearward pad section having a rear edge and a rear width between rear side edges, wherein at least a portion of the rear width is equal to at least a portion of the forward width;
   the forward pad section having a forward pad length measured from the front edge along the longitudinal dimension to the location of the absorptive pad that delineates the forward pad section from the rearward pad section; and
   the rearward pad section having a rear length measured along the longitudinal dimension from the rear edge to the location of the absorptive pad,
   wherein a location separates the forward pad section from the rearward pad section;
   wherein the rear width decreases in a continuous manner along the longitudinal dimension as the width approaches the rear edge, the forward width decreases in a continuous manner from the location to the front edge, and the decrease in the rear width is larger than the decrease in the forward width;
   wherein the rear width is large enough to prevent the rear side edges from sliding into and resting within the crease between the buttocks; and
   wherein the length of the absorptive pad is such that at least a portion of the rearward pad section covers the buttocks of the user when the absorptive pad is in use.

2. The absorptive pad of claim 1, wherein the rearward pad section is integral with the forward pad section.

3. The absorptive pad of claim 2, wherein the rear width at the rear edge is at least 50 percent narrower than the forward width at the forward edge.

4. The absorptive pad of claim 1, wherein a portion of each of the forward side edges forms a concave curve.

5. The absorptive pad of claim 1, wherein the rear width comprises a width such that the pad covers at least a portion of each of a user's buttocks, as well as a crease between the buttocks.

6. The absorptive pad of claim 1, wherein the absorptive pad comprises a continuously decreasing width, so that the forward width decreases from the front edge to the location, and the rear width continues to decrease from the location to the rear edge.

7. The absorptive pad of claim 1, wherein the absorptive pad comprises functional zones.

8. An article comprising an absorptive pad according to any one of claims 1 to 5 or 6 to 7.

9. The article of claim 8, wherein the article is a protective undergarment.

* * * * *